United States Patent [19]
Hickox

[11] Patent Number: 6,019,821
[45] Date of Patent: Feb. 1, 2000

[54] METHOD AND APPARATUS FOR REMOVING CONDENSATE FROM COMBUSTION ANALYZER SAMPLE

[75] Inventor: Richard M. Hickox, Ross Township, Allegheny County, Pa.

[73] Assignee: Bacharach, Inc., Pittsburgh, Pa.

[21] Appl. No.: 09/091,925

[22] PCT Filed: Jan. 15, 1997

[86] PCT No.: PCT/US97/00840

§ 371 Date: Jun. 24, 1998

§ 102(e) Date: Jun. 24, 1998

[87] PCT Pub. No.: WO97/26067

PCT Pub. Date: Jul. 24, 1997

Related U.S. Application Data

[60] Provisional application No. 60/009,948, Jan. 16, 1996.

[51] Int. Cl.[7] .................................................. B01D 45/04
[52] U.S. Cl. .................................. 95/272; 55/441; 55/449
[58] Field of Search ............................ 95/261, 262, 269, 95/272; 96/191, 212, 192, 208, 216; 55/441, 449, 448, 450; 137/171, 177, 203, 204

[56] References Cited

U.S. PATENT DOCUMENTS

| | | | |
|---|---|---|---|
| 2,043,944 | 6/1936 | Baker et al. .............................. | 55/441 |
| 3,315,448 | 4/1967 | Nicolas ..................................... | 55/441 |
| 3,525,196 | 8/1970 | Brieskorn ................................. | 95/261 |
| 3,680,388 | 8/1972 | Critchley et al. .................... | 73/863.11 |
| 4,461,183 | 7/1984 | Wedding .................................. | 55/449 |
| 4,769,050 | 9/1988 | Shaw et al. .............................. | 55/441 |
| 5,018,395 | 5/1991 | Hickox et al. ....................... | 73/864.34 |
| 5,240,486 | 8/1993 | Springmann et al. ................... | 55/320 |
| 5,334,239 | 8/1994 | Choe et al. .............................. | 95/261 |

*Primary Examiner*—Duane S. Smith
*Attorney, Agent, or Firm*—Webb Ziesenheim Logsdon Orkin & Hanson, P.C.

[57] ABSTRACT

A trap for removing moisture from sampled gases containing moisture in vapor and/or entrained liquid form includes an elongate conduit having a plug substantially centrally positioned therein to prevent flow directly through the conduit, the conduit being provided with a radially directed hole on each side of the plug. A tube is substantially concentric with the conduit and has stoppers at opposite ends thereof with openings therein for the conduit to pass therethrough. At least one of the stoppers is provided with a second opening which can be stopped during sampling and unstopped for draining. During sampling, sample gases are drawn into one end of the conduit and exhausted radially into the space between the conduit and the tube such that vapor condenses on the inner surface of the tube, entrained liquid collects on the inner surface and the gas enters the conduit on the other side of the plug and exhausts to an analyzer.

7 Claims, 1 Drawing Sheet

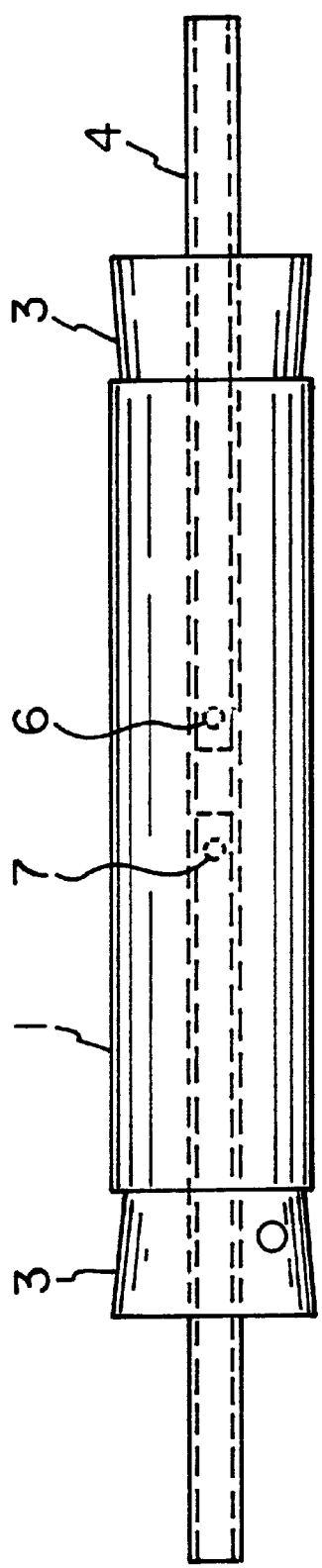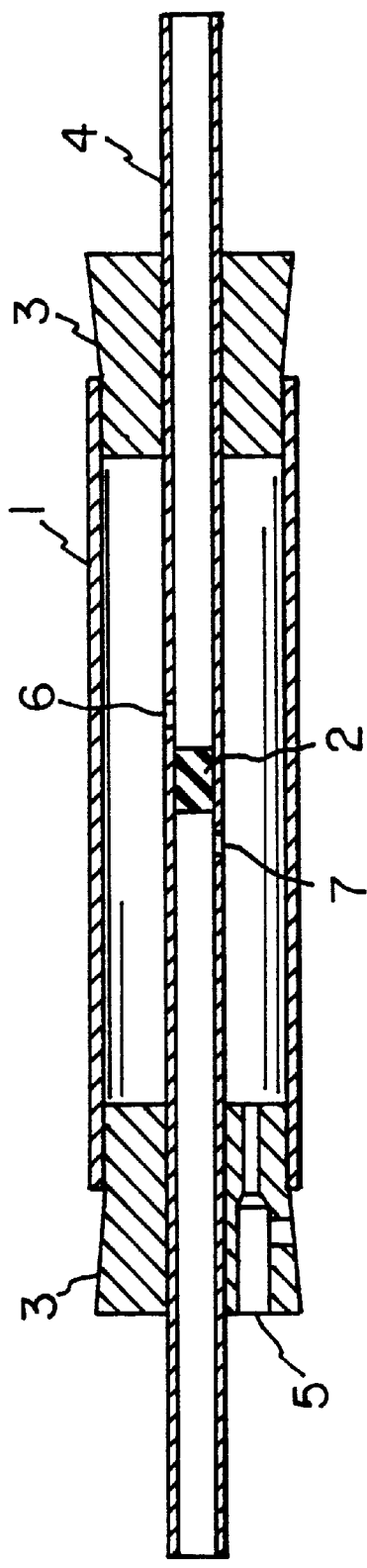

METHOD AND APPARATUS FOR REMOVING CONDENSATE FROM COMBUSTION ANALYZER SAMPLE

CROSS-REFERENCE TO RELATED APPLICATION

This application is the national phase of International Application PCT/US97/00840, filed Jan. 15, 1997, which claimed the benefits of U.S. Provisional Application No. 60/009,948, filed Jan. 16, 1996.

FIELD OF THE INVENTION

This invention pertains to the field of gas analysis, particularly, flue gas analysis and, specifically, to removal of moisture from the sample gases prior to analysis.

BACKGROUND OF THE INVENTION

In order to analyze flue gases, for example, it is necessary to draw moisture laden gases into the sampling system. The moisture may be in the form of vapors or entrained liquid. The moisture in the gases, when it condenses, damages pumps and sensors interfering with the analysis. Since the analysis may be made at the location of a home furnace by furnace repairmen that carry all equipment to the location of testing, there exists the need for a simple, rugged piece of equipment for removing moisture from flue gases prior to analysis.

An example of a gas sampling device is disclosed in U.S. Pat. No. 5,018,395 entitled "Gas Sampling Device With Improved Mixed Flow Fan" assigned to the same assignee as this application.

Present solutions to the moisture problem are not satisfactory. One solution replaces a reciprocating pump with a mixed flow or centrifugal fan which can pass the condensate, however, this does not solve the problem of the moisture in the analyzer. Moreover, the suction that can be drawn by a centrifugal fan is typically limited to a 1 inch water column. Another solution is to pass the sample through a desiccant. The desiccant needs to be replaced hourly in currently used volumes, say, a liter per minute. The desiccant must then be reactivated by heating in an oven.

A complicated apparatus for condensing moisture from flue gas prior to analysis is disclosed in U.S. Pat. No. 3,680,388. Another apparatus for mechanically removing moisture from flue gases is disclosed in U.S. Pat. No. 5,240,486. In the latter device, flue gas is drawn in a tube and axially exhausted against a plate and then drawn into yet a larger volume before being exhausted to the analyzer.

It is an advantage of the moisture trap, according to this invention, that it is extremely simple to manufacture and use. The trap can be positioned in any orientation and still effectively trap moisture. Moreover, it is easily and quickly drained and returned to service.

Briefly, according to this invention, there is provided a moisture trap for removing moisture from sampled gases containing moisture in vapor and/or entrained liquid form. The trap comprises a small diameter elongate tubular conduit having a plug centrally positioned therein to prevent flow directly through the conduit. The conduit is provided with two radially directed holes, one positioned on each side of the plug and adjacent thereto, say, within ½ inch. A large diameter tube substantially concentric with the elongate tubular conduit is secured in place by plugs at each end thereof with openings therein for the elongate tubular conduit to pass therethrough. At least one of the plugs is provided with a second passage therethrough that can be stopped during sampling and unstopped for draining. The plug in the elongate tubular conduit is positioned to be approximately halfway between the plugs in the ends of the large diameter tube. Thus, during sampling, sample gases are drawn into one end of the elongate tubular conduit, exhausted radially into the space between the conduit and the tube such that vapor condenses on the inner surface of the tube and entrained liquid collects on the inner surface. The gas then re-enters the conduit on the other side of the plug and exhausts to the analyzer. Regardless of the orientation of the trap, it can accumulate liquid up to about 40% of its volume prior to requiring draining. Preferably, the radial holes in the elongate tubular conduit are positioned 180° opposite to each other.

BRIEF DESCRIPTION OF THE DRAWINGS

Further features and other objects and advantages will become clear from the following detailed description made with reference to the drawings in which:

FIG. 1 is a side view of a moisture trap according to this invention; and

FIG. 2 is a section view through a moisture trap according to this invention.

DESCRIPTION OF THE PREFERRED EMBODIMENT

Referring now to FIGS. 1 and 2, a large diameter tube 1 which may, for example, comprise a 1 inch tube of clear polycarbonate, is provided with end stoppers or plugs made of rubber 3. The rubber end stoppers have an axially or centrally positioned passage therethrough for receiving a stainless steel tubing. The stainless steel tubing has a rubber plug 2 positioned therein. On each side of the plug and adjacent thereto are radial openings through the wall of the stainless steel tubing 6 and 7. At least one of the end plugs is provided with a passage 5 into which a drain plug or valve may be inserted.

The sample gas (and condensate formed during the passage of the sample from the flue to the trap) enters the stainless steel tubing 4 from either end. It is interrupted by the plug 2 and exits radially to the space between the stainless steel tubing and the large diameter tube to cool further and to trap the condensate. The cool saturated sample re-enters the stainless steel tubing on the opposite side of the plug and flows out to the analyzer pump through the tubing.

The above-described apparatus has been tested in the laboratory. The trap had a 1 inch diameter tube with an axial space of about 3½ inches between plugs. Flue gases having a dew point of 130° and at a temperature of about 400° to 600° F. were passed through the trap. In about 80 minutes, approximately 40% of the volume of the trap was filled with liquid. The liquid could be drained from the trap by removal of the plug within about 15 seconds.

It is not essential that the tubing and large diameter tube be cylindrical in cross section. Other cross sections are suitable. The size of the larger tube can vary. It is important that the inner surface of the tube have an adequate area for transmitting heat outwardly. The materials from which the tube and tubing are fabricated are not critical. The stoppers and plug in the tubing may be rubber or any other elastomeric material that will be resilient at temperatures encountered.

Having described presently preferred embodiments of the invention, it is to be understood that it may be otherwise embodied within the scope of the appended claims.

I claim:

1. A trap for removing moisture from sampled gases containing moisture in vapor and/or entrained liquid form comprising:
   a) an elongate conduit having a plug substantially centrally positioned therein to prevent flow directly through the conduit, said conduit being provided with a radially directed hole on each side of the plug adjacent thereto; and
   b) a tube being substantially concentric with said conduit and having stoppers at opposite ends thereof with openings therein for the conduit to pass therethrough, at least one of the stoppers being provided with a second opening which can be stopped during sampling and unstopped for draining,
   whereby, during sampling, sample gases are drawn into one end of said conduit and exhausted radially into the space between the conduit and the tube such that vapor condenses on the inner surface of the tube, entrained liquid collects on the inner surface and the gas enters the conduit on the other side of the plug and exhausts to an analyzer.

2. A trap as set forth in claim 1 wherein the conduit is tubular and the tube is cylindrical.

3. A trap as set forth in claim 2 wherein the conduit is of small diameter relative to the diameter of the tube.

4. A trap as set forth in claim 1 wherein the radially directed holes in the elongate conduit are positioned 180° to each other.

5. A trap as set forth in claim 1 wherein the conduit is stainless steel, the tube is clear polycarbonate and the plug and stoppers are rubber.

6. A trap as set forth in claim 5 wherein the tube is 1" in diameter and includes an axial space of about 3½" between stoppers.

7. A method for removing moisture from sampled gases containing moisture in vapor and/or entrained liquid form comprising the steps of:
   a) drawing gases to be sampled into one end of an elongate conduit having a plug approximately midway in its length;
   b) exhausting the gases radially through a hole in the conduit on one side of the plug into a space between the conduit and a larger tube;
   c) maintaining the larger tube at a temperature below the dew point of the sampled gases such that vapor condenses on an inner surface of the tube and entrained liquid collects on the inner surface;
   d) redrawing the gases from the space between the conduit and the larger tube radially through a hole in the conduit on the opposite side of the plug into the conduit; and
   e) exhausting the gases to the analyzer for analysis.

* * * * *